United States Patent
Spahn

(10) Patent No.: US 9,031,197 B2
(45) Date of Patent: May 12, 2015

(54) METHOD FOR DETECTING THE TRUE COINCIDENCE OF TWO CHARGE PULSES ON ADJACENT PICTURE ELEMENTS, X-RAY DETECTOR AND X-RAY IMAGE RECORDING APPARATUS

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 452 days.

(21) Appl. No.: 13/562,236

(22) Filed: Jul. 30, 2012

(65) Prior Publication Data
US 2013/0028382 A1     Jan. 31, 2013

(30) Foreign Application Priority Data

Jul. 29, 2011  (DE) .......................... 10 2011 080 077

(51) Int. Cl.
| | |
|---|---|
| *G01T 1/172* | (2006.01) |
| *G01T 1/24* | (2006.01) |
| *G01N 23/04* | (2006.01) |
| *H04N 5/32* | (2006.01) |
| *G01T 1/20* | (2006.01) |
| *G01T 1/29* | (2006.01) |

(52) U.S. Cl.
CPC ............... *G01T 1/172* (2013.01); *G01T 1/247* (2013.01); *G01T 1/2018* (2013.01); *G01N 23/04* (2013.01); *G01T 1/2928* (2013.01); *H04N 5/32* (2013.01)

(58) Field of Classification Search
CPC ....... G01T 1/247; G01T 1/172; G01T 1/2018; G01T 1/2928; H04N 5/32; G01N 23/04
See application file for complete search history.

(56) References Cited

U.S. PATENT DOCUMENTS

| | | | |
|---|---|---|---|
| 6,559,453 B2 | 5/2003 | Lundqvist | 250/371 |
| 7,208,739 B1 | 4/2007 | Yanoff et al. | 250/363.09 |
| 2006/0086913 A1* | 4/2006 | Spahn | 250/580 |
| 2010/0025593 A1* | 2/2010 | Proksa | 250/370.09 |
| 2010/0213353 A1* | 8/2010 | Dierickx | 250/214 R |
| 2011/0210235 A1* | 9/2011 | Dierickx | 250/214 R |
| 2012/0280132 A1* | 11/2012 | Nakamura et al. | 250/368 |
| 2012/0305786 A1* | 12/2012 | Dierickx | 250/371 |
| 2014/0197307 A1* | 7/2014 | Jorion | 250/252.1 |

FOREIGN PATENT DOCUMENTS

DE  10 2004 048 962 A1   4/2006   ............ G03B 42/02

OTHER PUBLICATIONS

Spahn, Martin, "Flat Detectors and Their Clinical Applications," Eur. Radiol., vol. 15, Springer-Verlag, 14 pages, Mar. 1, 2005.

* cited by examiner

*Primary Examiner* — Michael Logie
(74) *Attorney, Agent, or Firm* — King & Spalding L.L.P.

(57) ABSTRACT

With the aid of discriminators on a picture element of an X-ray detector, digital outputs are generated that indicate energy intervals to which X-ray quanta are allocated. If this occurs for adjacent picture elements, a distinction may be made between true coincidences, in which k-fluorescence photons play a part, and random coincidences in which two primary quanta randomly strike adjacent picture elements. The energy of the primary quantum may also be at least roughly reconstructed in the case of true coincidences. An energy-triggering measurement may thereby be provided to the extent that different materials of a picture object should be distinguished.

4 Claims, 4 Drawing Sheets

US 9,031,197 B2

METHOD FOR DETECTING THE TRUE COINCIDENCE OF TWO CHARGE PULSES ON ADJACENT PICTURE ELEMENTS, X-RAY DETECTOR AND X-RAY IMAGE RECORDING APPARATUS

CROSS-REFERENCE TO RELATED APPLICATIONS

This application claims priority to German Patent Application No. 10 2011 080 077.8 filed Jul. 29, 2011. The contents of which is incorporated herein by reference in its entirety.

TECHNICAL FIELD

This disclosure relates to a method for detecting the true coincidence of two charge pulses, simultaneously detected in accordance with a predefined criterion, on adjacent picture elements of an X-ray detector. It also relates to an X-ray detector and to an X-ray image recording apparatus having the same.

BACKGROUND

The present case relates in particular to such X-ray detectors and their use which comprise a layer converting X-rays (quanta) into a plurality of charge carrier pairs, what are known as directly converting X-ray detectors. Charge carriers of the charge carrier pairs (typically under the effect of an electrical field) thus namely form a charge pulse, and if the X-ray detector comprises a plurality of picture elements (which correspond to pixels of an X-ray image to be produced), then as a rule such charge pulses strike a single picture element. The present case involves a deviation from this rule: if the individual X-ray quanta comprise energy levels above what is known as the k-edge (for example 27 keV for Cd, 32 keV for Te), then k-fluorescence dominates in the case of the photo effect. A k-fluorescence photon is re-emitted in addition to the photoelectron, and this has roughly the energy of the k-edge, or, more precisely, the difference in the binding energy levels of the k-shell and the shell from which a succeeding electron originates. Owing to the not inconsiderable mean free path length of the k-fluorescence photon of about 100 μm or 60 μm respectively for Cd or Te respectively, in addition to the two cases where the k-fluorescence photon is reabsorbed by the same picture element as the primary photon or it completely leaves the detector material, the case may accordingly also occur where in a neighboring picture element it is reabsorbed to the picture element reabsorbing the primary photon.

The case of reabsorption in a neighboring picture element, which is substantially more probable than the k-fluorescence photon not being absorbed at all in the detector material, accordingly leads to two events being detected and the energy of the primary quantum being divided over the two picture elements.

If there is a desire to detect the energy levels of the X-ray quanta and count them, then the occurrence of the k-fluorescence photon is disruptive.

There is consequently a desire to detect the coincidence of two charge pulses on adjacent picture elements in order to be able to correct the count values or the detected energy levels. There is therefore firstly an attempt in accordance with a predefined criterion to detect whether two charge pulses occur simultaneously on adjacent picture elements anyway. However, it should accordingly also be ensured that this involves a true coincidence, i.e. the same event, and not, for instance, a false coincidence, i.e. the random simultaneous striking of two primary X-ray quanta in adjacent picture elements.

Two different approaches have previously been taken in this regard:

In the case of a conventional approach discussed first an analog coincidence circuit is provided (before the analog-digital conversion) which connects each picture element to its directly neighboring picture elements and, in the case of two events being simultaneously detected in accordance with a predefined criterion, is capable of totaling the energy of the two events in an analog manner before this is converted to digital. The advantage of this is that the energy is correctly output (is restored), and if true coincidence is a prerequisite, the correct number of X-ray quanta is also counted. The drawback of the analog coincidence circuits lies in that these are highly complex, in that namely highly integrated silicon technology is required for their implementation. They also consume a lot of energy, so cooling of the X-ray detector is a challenge.

Previously discussed in the field as a second approach is the idea of using a digital coincidence circuit (i.e. following analog-digital conversion), wherein this merely has a veto function: if two adjacent picture elements respond then one of the two count values is disregarded. The advantage lies in the fact that the circuit is significantly simpler and in that the correct number of quanta is counted if true coincidence is assumed. The drawback lies in that the energy of the absorbed quantum cannot be reconstructed (restored) since the energy of the quantum from one of the two picture elements is disregarded.

SUMMARY

In one embodiment, a method is provided for detecting the true coincidence of two charge pulses, simultaneously detected in accordance with a predefined criterion, on adjacent picture elements of an X-ray detector, wherein the height of the charge pulses is allocated to one of at least three intervals respectively and information about the allocation is provided in digital form, and in that the combination of the allocations of the charge pulses detected by the two adjacent picture elements to one of the intervals is then checked for whether or not it is a member of a predefined subset of possible combinations, and in that a true coincidence is determined or not as a function of this membership.

In a further embodiment, when detecting a true coincidence a count value is changed for a number of provided allocations to one of the intervals in the case of at least one of the picture elements. In a further embodiment, in the case of those of the adjacent picture elements with the allocation to an interval for lower heights the associated count value is reduced by one and in the case of the other of the adjacent picture elements the count value is reduced by one in a first interval and is increased by one in a second interval. In a further embodiment, the charge pulses are generated in a certain material in which X-ray quanta generated by k-fluorescence have a predefined maximum energy, and wherein the intervals are selected such that charge pulses tracing back to X-ray quanta generated by k-fluorescence are detected in one of the intervals, and in that due to the X-ray quanta directly generated by an X-ray source are detected in one of the other intervals.

In another embodiment, an X-ray detector has a layer converting X-rays into charge carrier pairs, so charge carrier pairs form a charge pulse, and having a plurality of picture elements which each comprise: a device for receiving a charge pulse and for outputting a voltage dependent on the height of the charge pulse, at least two discriminators for comparing the output voltage with at least one threshold value ($V_{thr1}$, $V_{thr2}$, $V_{thr3}$ and $V_{thr4}$, respectively and for outputting a digital signal as a function of the respective comparison, a counter for each discriminator for counting certain signals, and a digital device for evaluating the count values thus obtained, wherein the digital devices of a plurality of picture elements are coupled to each other to detect coincidences.

In a further embodiment, the digital devices of a picture element are designed to change count values in counters. In a further embodiment, the digital devices of a picture element are designed to change the count value of one of the counters associated with this picture element on the one hand and at the same time to change the count value of one of the counters associated with a picture element adjacent to this picture element on the other hand. In a further embodiment, the discriminators are window discriminators. In a further embodiment, the layer includes cadmium telluride or cadmium zinc telluride.

In another embodiment, an X-ray image recording apparatus includes any of the X-ray sources and X-ray detectors disclosed above.

BRIEF DESCRIPTION OF THE DRAWINGS

Example embodiments will be explained in more detail below with reference to figures, in which.

DETAILED DESCRIPTION

Figure 1:
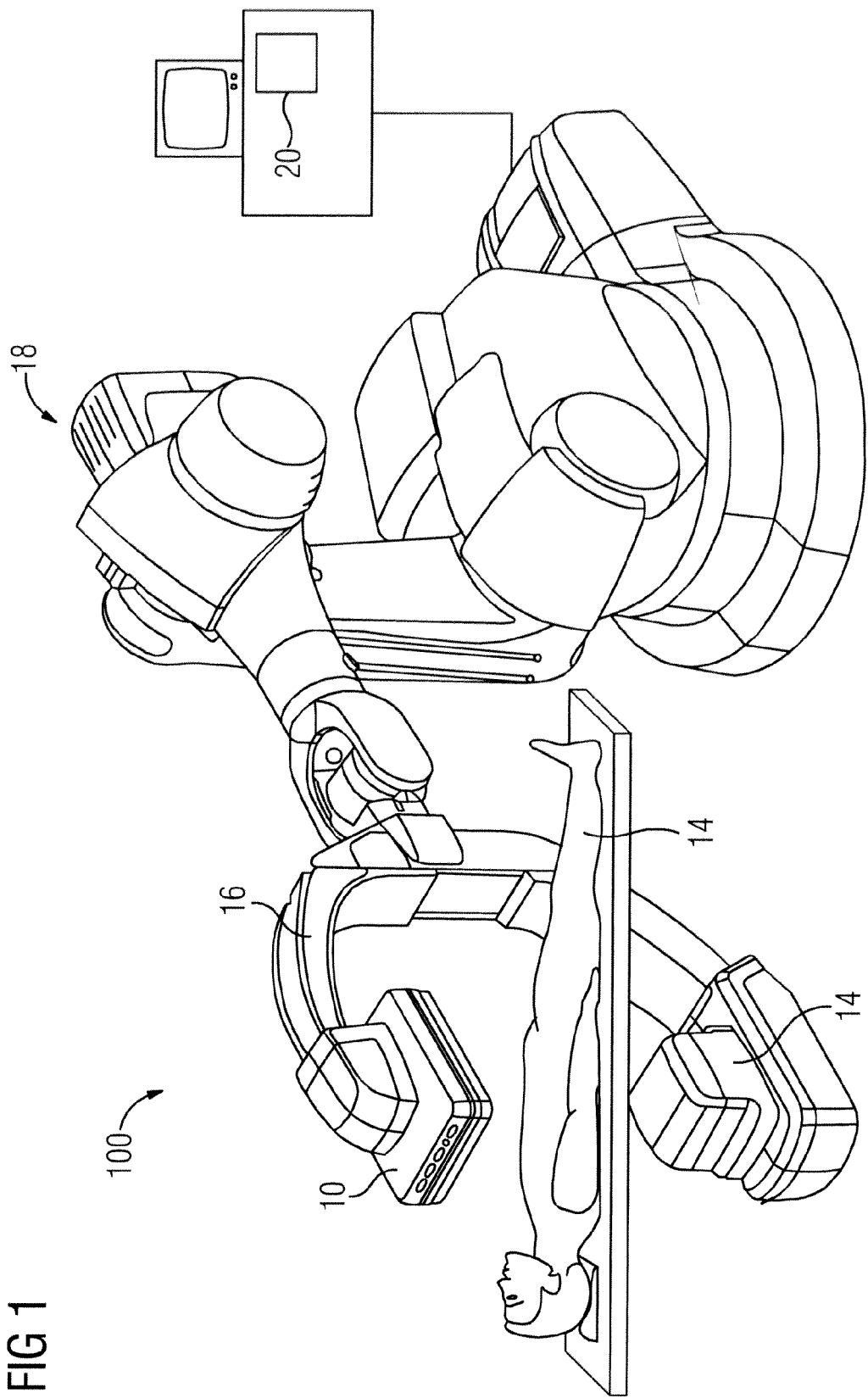
FIG. 1 shows an X-ray image recording apparatus in which an X-ray detector can be used, according to an example embodiment.
Figure 2:
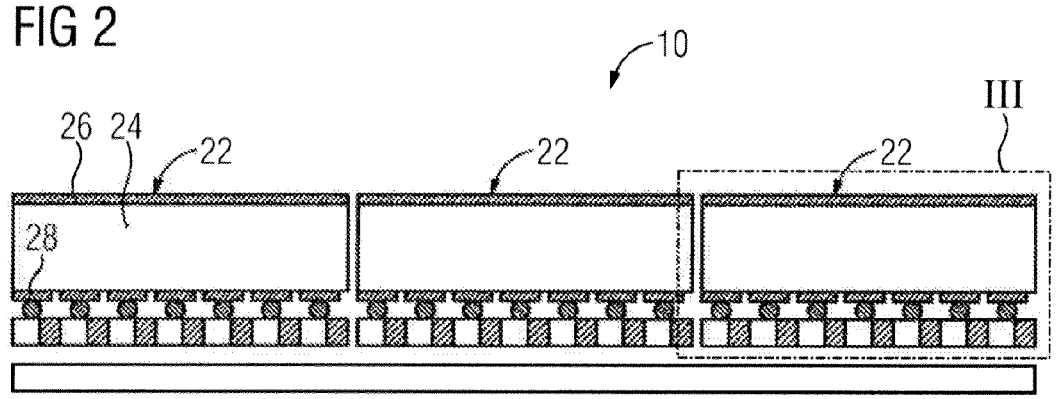
FIG. 2 shows a section through an example X-ray detector having a plurality of tiles, according to an example embodiment.

Some embodiments provide a method for detecting the coincidences of the type mentioned in the introduction and to also provide an X-ray detector for this, with the aid of which correct counting of the quanta is enabled as is reliable detection of the energy.

In some embodiments the height of the charge pulses is therefore allocated to one of at least three intervals respectively, and information about this allocation is provided in digital form. The combination of the allocations of the charge pulses detected by the two adjacent picture elements to one of the intervals is accordingly checked for whether it is a member of a predefined subset of possible combinations or not. A coincidence is determined (detected) or not as a function of this membership.

If the first interval is used to distinguish a charge pulse from noise, then two intervals are involved which represent charge pulses of different heights above the noise. With suitable selection of the intervals it may therefore be determined whether the charge pulse (more likely) belongs to a primary X-ray quantum or to a k-fluorescence quantum. If two charge pulses are involved, both of which are each allocated to an interval with the higher height, i.e. are both allocated with the aid of threshold values which are higher than the threshold values in the case of two other intervals, then neither of the two charge pulses appears to be generated by a k-fluorescence quantum; the combination of the allocation into the respectively higher interval in the case of the two picture elements is then an indication that a coincidence cannot be determined. On the other hand a coincidence may be determined if one charge pulse is in the higher interval and the other one is in the middle interval, i.e. the lower interval above the noise.

Certain embodiments make use of the fact that the information about the allocation must be provided in digital form, although the energy itself does not have to be. Rough division into a plurality of energy intervals is enough to be able to make sufficiently accurate statements. A small number of intervals is sufficient in particular for the purpose of energy discrimination to distinguish different materials that are penetrated by the X-rays. Exact measurement of the energy is not necessary.

In one embodiment a count value for a number of provided allocations to one of the intervals is changed in the case of at least one of the picture elements when detecting a coincidence. In this aspect the method is based on the recognition that a k-fluorescence photon should not be incorrectly allocated to a picture element.

The associated count value may therefore be reduced by one in the case of those of the adjacent picture elements with the allocation to an interval for lower heights (with the assumption of substantially equal intervals for all picture elements). The k-fluorescence photon is not included in the count therefore. At the same time, in the case of the other of the adjacent picture elements the count value may be reduced by one in a first interval and is increased by one in a second interval, which represents higher values of the charge pulse height. With suitable selection of the intervals the energy of the k-fluorescence photon is added to the adjacent picture element in this aspect, so the energy from the second interval is the correct one to be allocated and not that in the first interval.

In one embodiment the charge pulses are generated in a certain material in that X-ray quanta generated by k-fluorescence have a predefined maximum energy. The intervals are then selected such that charge pulses tracing back to X-ray quanta generated by k-fluorescence are detected in one of the intervals, and the charge pulses directly generated by an X-ray quantum are detected in at least one of the other intervals.

The energy levels of the k-fluorescence photons are below 29 keV in particular in the case of CdTe. However, owing to the acceleration voltage in the X-ray tubes and by way of suitable filtering, it may be ensured that no energy levels below 30 keV occur with primary quanta. If the line is accordingly drawn at 29 keV, then only k-fluorescence photons ensure counting of a count value in the interval, which ends with 29 keV, and only primary quanta ensure counting of count values in one of the higher intervals.

The intervals may therefore be particularly favorably selected with sufficient suitability of the direct converter. PbO, $PbJ_2$ and $HgJ_2$ are also suitable as direct converters in addition to CdTe or even CdZnTe.

In addition to the layer converting the X-rays into the charge carrier pairs the X-ray detector comprises a plurality of picture elements, and the picture elements in turn each comprise:

a device for receiving a charge pulse and for outputting a voltage dependent on the height of the charge pulse, at least two discriminators for comparing the output voltage with at least one threshold value respectively (so a distinction can be made between three intervals) and for outputting a digital signal as a function of the respective comparison, a counter for each discriminator for counting certain digital signals (namely as a rule the number of ones output), and finally a digital device for evaluating the count values, wherein the digital devices of a plurality of picture elements are coupled to each other to detect coincidences.

Detection can take place in particular according to the method disclosed herein by comparison of the allocations to an interval with the aid of discriminators.

The X-ray detector disclosed herein therefore provides for a rough measurement of the energy with the aid of the discriminators, wherein the rough measurement may be sufficient enough that a distinction can be made between k-fluorescence quanta and primary quanta and the count results can be allocated so the coincidence can be detected. This is also made possible by the coupling of the digital devices of a plurality of picture and point elements to each other.

In one embodiment of the X-ray detector the digital devices of a picture element are designed to change count values in counters. Thus, counting can be corrected when detecting a coincidence.

This may not only include the digital devices of a picture element being designed to change the count values of the counter associated with this picture element but at the same time also change a picture element adjacent to this picture element. This embodiment of the method can be implemented in this way in which the energy of the k-fluorescence quantum is also counted in the case of the adjacent picture element and is added to the primary quantum previously reduced by this energy to detect the original energy.

In one embodiment of the X-ray detector the discriminators are window discriminators, i.e. use upper and lower threshold values. Precisely one interval may thus be determined by each discriminator. If the lower threshold value relating to all discriminators is set so as to be greater than zero, then a further interval between zero and this lower threshold value is also indirectly detected as well.

As already stated above, the layer may comprise CdTe or CdZnTe, so the energy levels of the k-fluorescence photons can be separated particularly well from those of the primary quanta.

Other embodiments provide an X-ray image recording apparatus having an X-ray source and an X-ray detector as disclosed herein. The X-ray image recording apparatus can also comprise a digital control and/or evaluation device which communicates with the digital devices and/or can read out the count values from the counters to detect an X-ray image which is energy-resolved.

ONE EMBODIMENT

An X-ray image recording apparatus can be an X-ray angiography system, which is designated 100 in FIG. 1, and comprises an X-ray detector 10 which receives X-rays from an X-ray source 12 which have penetrated a patient 14 or another image object. In the present case the X-ray source 12 and the X-ray detector 10 are suspended on a C-arm 16 which is guided by a six-axis jointed arm robot 18. This all takes place under the control of a controller 20, which is simultaneously used as an evaluation device for evaluating the data from the X-ray detector 10.

The X-ray detector 10 comprises a plurality of tiles 22 which each have a layer 24 made from detector material and which can comprise for example CdTe or CdZnTe. Each tile comprises an upper electrode 26, and there is a plurality of picture elements for each tile with an anode 28 being allocated to each of these. When a voltage is applied between anode 28 and cathode 26 X-ray quanta hv can be detected because the layer 24 converts these into charge carrier pairs and these charge carrier pairs are separated by the voltage, and for example the electrons arrive at the anode 28 of a picture element. The anodes 28 are coupled by an electrical connection 30 to application specific integrated circuits ("ASICs, Application Specific Integrated Circuit") 32.

Figure 3:
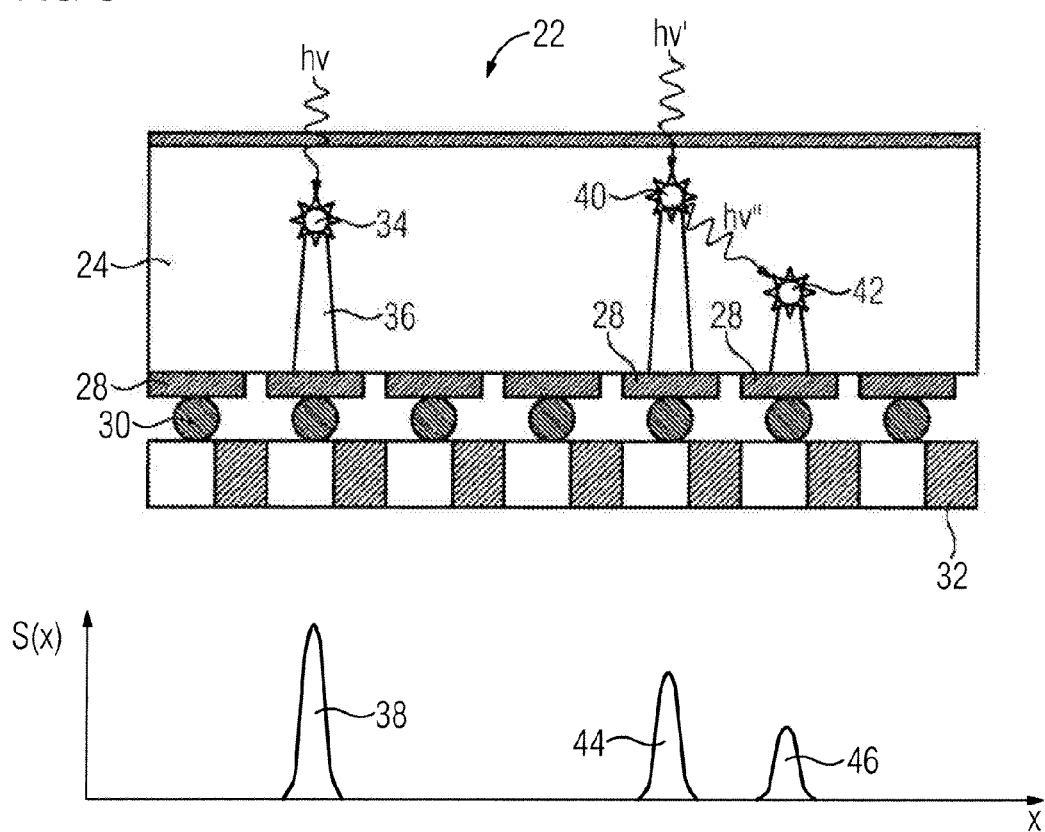
FIG. 3 shows a detail III from FIG. 2 having an enlarged tile, with the aid of which the occurrence of a k-fluorescence quantum is explained, according to an example embodiment.

It shall now be explained with the aid of FIG. 3 what the k-fluorescence is about.

The X-ray quantum hv shown on the left in FIG. 3 passes into the layer 24 and generates charge carrier pairs in a point 34 there and these are transported via the path 36 to the associated anode 28 of one of the picture elements and are detected by the picture element. A pulse 38 is allocated to the X-ray quantum hv.

An X-ray quantum hv' can accordingly have sufficiently high energy such that k-fluorescence occurs: in addition to generating charge carrier pairs, starting from source point 40 a k-fluorescence quantum hv'' is emitted which, starting from point 42, generates charge carrier pairs which then likewise arrive at an anode 28 of a picture element. As may be seen from FIG. 3, the charge carrier pairs pass from the region 40 to one of the anodes 28, to one of the picture elements, and the charge carrier pairs from the region 42, which go back to the k-fluorescence photon hv'', arrive at another anode 28, which leads to a different picture element. The X-ray quantum hv' thus causes two pulses to be measured, namely pulses 44 and 46.

Certain embodiments accordingly deal with the fact that the same event (namely the same original X-ray quantum hv') is to be allocated to the two pulses 44 and 46 and the correct energy allocated to this, which roughly corresponds to the height of the total of the two pulses 44 and 46.

Figure 4:
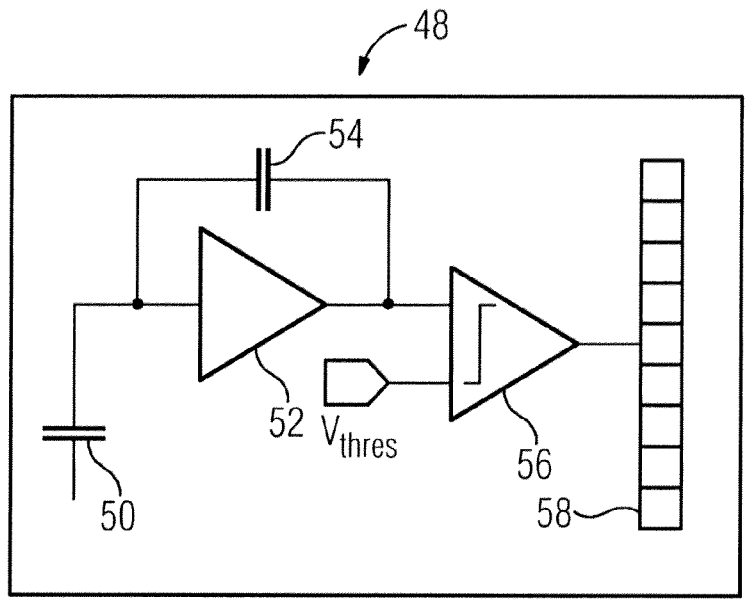
FIG. 4 shows a counting picture element to explain the basic mode of operation of such, according to an example embodiment.

FIG. 4 shows a single picture element 48. The detector input 50 detects the charge pulses, and these are amplified in an amplifier 52, a stabilization of the signals being possible by way of a capacitor 54. The amplified signal is accordingly compared with a voltage $V_{thres}$ or supplied to a discriminator 56 respectively, and if the voltage $V_{thres}$ is exceeded a digital counter 58 registers a counting event. The counter 58 gradually counts a count value higher and higher until it is deleted from outside.

Figure 5:
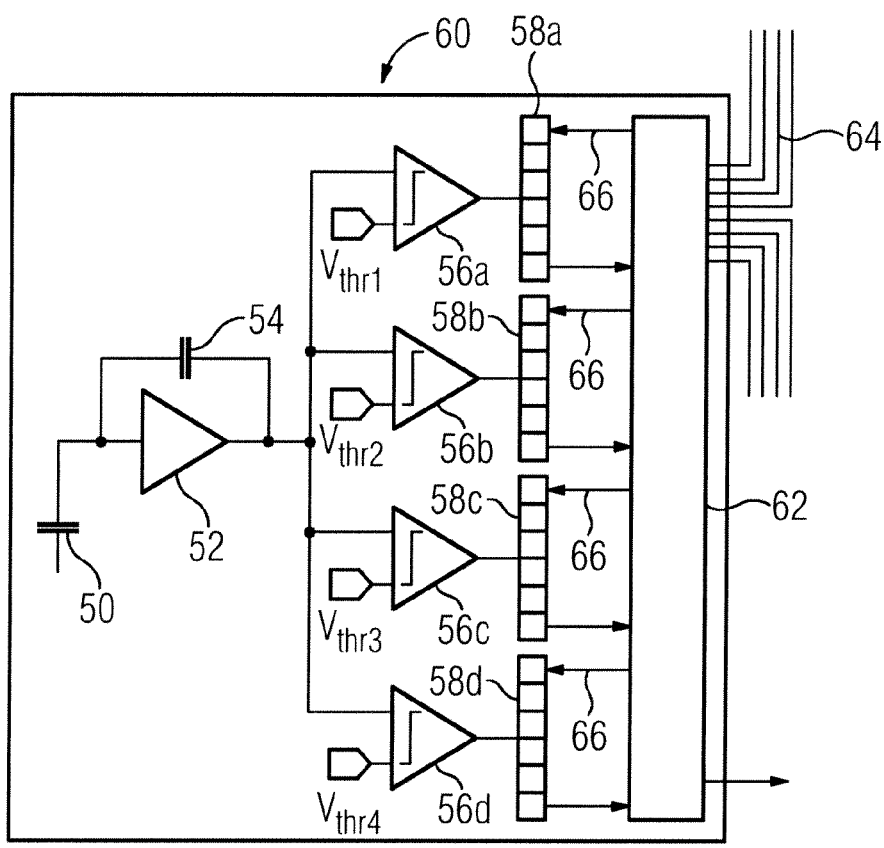
FIG. 5 shows a counting picture element with the capacity for energy resolution, according to an example embodiment.
Figure 6:
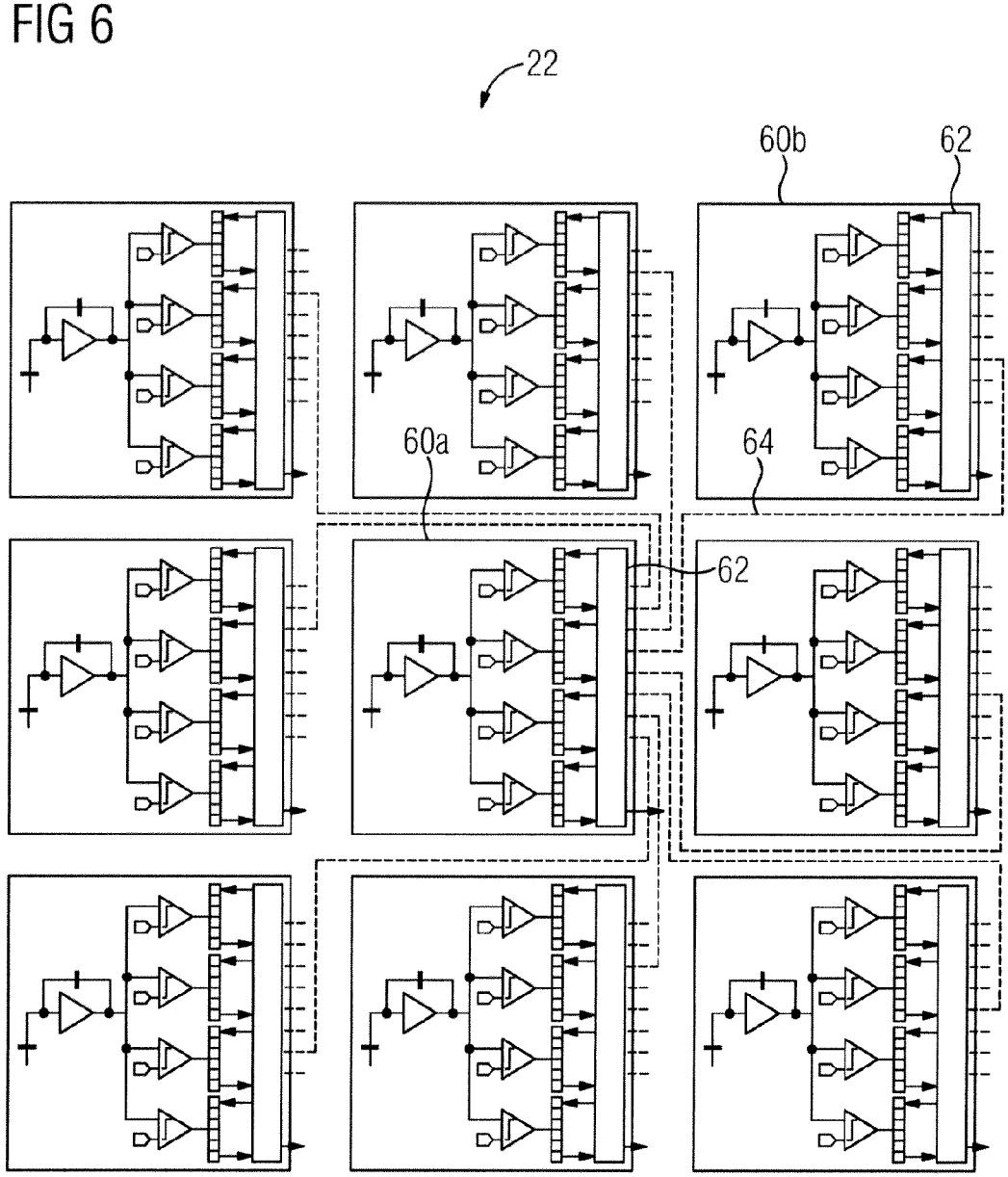
FIG. 6 shows and arrangement of the picture elements from FIG. 5, according to an example embodiment.

FIG. 4 shows the basic principle of a picture element 48 that is used in the present case. FIG. 5 accordingly shows a picture element 60 as is actually used in the present case.

Instead of a single discriminator 56 there is a plurality of discriminators 56a, 56b, 56c, 56d in the present case, which may for instance be a number equal to $2^n$, where n is a whole number. Each discriminator 56a compares the input signal, which has been amplified by the amplifier 52, with two threshold values, wherein in the present case only one threshold value $V_{thr1}$, $V_{thr2}$, etc. is illustrated; it must merely be imagined that the upper threshold value of the discriminator 56a is exactly equal to the lower threshold value $V_{thr2}$ of the discriminator 56b, just as the upper threshold value of the discriminator 56b is the lower threshold value $V_{thr}$ of the discriminator 56c, etc.

Events which are energy-resolved are then measured in the counters 58a, 58b, 58c, 58d. The height of the charge pulses 36 and 44 respectively and 46 corresponds to the energy of the X-ray quanta hv, hv' without hv'' and hv'''. The voltage issuing from the amplifier 52 is for its part proportional to this height. If it generates a voltage above $V_{thr1}$, each event ensures counting in one of the counters 58a, 58b, 58c and 58d.

The energy intervals are also called "bins".

In the present case the counters 58a, 58b, 58c, 58d are coupled to a read and write logic (a digital device) 62 which for its part is coupled to the corresponding read logics of other pixels adjacent to the present picture element 60, see the lines 64. Data values (information) can be exchanged via the lines 64, so, by way of example, the digital device 62 of a picture element 60a knows that an event has been simultaneously detected in an adjacent picture element 60b. The simultaneousness is defined by the suitable selection of a time slot which is predefined by an internal clock. Both counts must fall within the time slot.

The only question is whether this simultaneous measurement can actually be attributed to a k-fluorescence quantum hv'', as has been described above with the aid of FIG. 3. As an alternative to this it would be possible for two primary X-ray quanta hv to strike purely randomly and for their energy to be completely deposited in the picture elements in each case. This distinction is possible in the present case in that coincidences with certain combinations of energy levels are involved.

If in the case of the material CdTe is accordingly selected by way of example for the layer 24, $V_{thr1}$ as 20 keV, $V_{thr2}$ as 40 keV, $V_{thr3}$ as 65 keV and $V_{thr4}$ as 90 keV, then the counters 58a, 58b, 58c and 58d measure the intervals from 20 to 40 keV, from 40 to 65 keV, from 65 to 90 keV and from 90 to 120 keV. By way of appropriate filtering it is also provided that the primary X-ray quanta have an energy level of more than 40 keV.

With true coincidences one of the two adjacent picture elements 60a, 60b will accordingly, as a rule, detect a measurement in interval 1, because the k-fluorescence quanta lie exactly in this first interval from 20 to 40 keV (namely roughly at about 27 keV). It is then not a matter of in which interval the respective other X-ray quantum is measured.

If, on the other hand, combinations are detected in which the two measurements lie in higher intervals, for instance they are both in the region of 40 to 65 keV, one in a region of 40 to 65 keV and the other in the region of 65 to 90 keV or of 90 to 120 keV, or finally one in the region of 65 to 90 keV and the other in the region of 90 to 120 keV, etc., then this is a false coincidence, i.e. a plurality of independent primary quanta are involved.

If a true coincidence is detected, as illustrated first above, the associated count value in the counter 58a is reduced by one by way of the digital device 62 of the picture element 60a, 60b, which detected the energy in the lower interval, and in the adjacent picture element 60a, 60b the measured value is likewise reduced where it last occurred and is increased by one in the respectively higher counter. If the picture element 60b has accordingly measured a count value in the associated counter 58a and if in the picture element 60a a counting event has been measured in the counter 58b and the count value has been increased by one, then the count value in the associated counter 58a of the picture element 60b is reduced by one as a correction for the occurrence of the k-fluorescence photon, which has landed on the picture element 60b, but in return, instead of the count value in the counter 58b, the event is added to the counter 58c, i.e. in picture element 60a, instead of the energy, which has ensured counting of an event by the counter 58b, this event is added to the counter 58c, i.e. the count value in the counter 58b is reduced by one and in return is increased by one in the next highest counter 58c.

In the present case correction of the count values is possible in that the digital devices 62 can have an effect on the counters 58a, see arrow 66, which allow digital overwriting of the count values.

With the aid of the X-ray detector 10 it is thus possible to measure in terms of energy resolution and segregate the effect of k-fluorescence photons in the process. The energy-resolved measurement is expedient by way of example if a distinction is to be made between two different materials, for instance the body tissue of the patient 14 and material foreign to the body. The different materials absorb X-rays in different ways, so the energy of the X-ray quanta, which strike the X-ray detector 10 and generate charge carrier pairs in the layer 24, is in each case dependent on which material they have passed through. A different energy field can therefore be allocated to individual picture elements. In the present case this is possible particularly precisely in that the effect of the k-fluorescence quanta is segregated. If different energy fields can accordingly be allocated, then the different material may also be reproduced in different ways in the X-ray image, by way of example by color imaging, or filtering can take place according to the specific material which is to be depicted. Other linear combinations or generally connections from image contents of certain energy fields are also conceivable. In the simplest case dual-energy imaging is conceivable.

Correct counting of the X-ray quanta on the one hand and at least a rough allocation of the energy levels on the other hand are therefore enabled by X-ray detector 10, wherein the rough allocation is sufficient to distinguish between different materials penetrated by X-rays issuing from the X-ray tubes 12.

What is claimed is:

1. A method for detecting a true coincidence of two charge pulses, simultaneously detected in accordance with a predefined criterion, on adjacent picture elements of an X-ray detector, comprising:
   allocating a height of the charge pulses to one of at least three intervals respectively,
   providing information about the allocation in digital form,
   analyzing a combination of the allocations of the charge pulses detected by the adjacent picture elements to one of the intervals to determine whether or not the combination is a member of a predefined subset of possible combinations, and
   determining the presence of a true coincidence based on the results of the analysis.

2. The method of claim 1, comprising changing a count value for a number of provided allocations to one of the intervals in the case of at least one of the picture elements.

3. The method of claim 2, comprising:
   for a first one of the adjacent picture elements allocated to an interval for a lower height, reducing a count value associated with the second picture element by one, and
   for a second one of the adjacent picture elements, reducing a count value associated with the second picture element by one in a first interval and increasing the count value associated with the second picture element by one in a second interval.

4. The method of claim 1, comprising:
   generating the charge pulses in a certain material in which X-ray quanta generated by k-fluorescence have a predefined maximum energy, and
   selecting the intervals such that charge pulses tracing back to X-ray quanta generated by k-fluorescence are detected in one of the intervals, and due to the X-ray quanta directly generated by an X-ray source are detected in one of the other intervals.

\* \* \* \* \*